United States Patent [19]

Boyle

[11] Patent Number: 4,720,570

[45] Date of Patent: Jan. 19, 1988

[54] RATE OF CRYSTALLIZING DIPHENYLISOPHTHALATE/DIPHENYL-TEREPHTHALATE MONOMER

[75] Inventor: Gerald M. Boyle, Syracuse, N.Y.

[73] Assignee: Celanese Corporation, New York, N.Y.

[21] Appl. No.: 840,352

[22] Filed: Mar. 14, 1986

[51] Int. Cl.$^4$ ............................................. C07C 67/52
[52] U.S. Cl. ....................................... 560/78; 562/486
[58] Field of Search ........................... 560/78; 562/486

[56] References Cited

U.S. PATENT DOCUMENTS 2,656,377 10/1953 Pino ........................................ 562/78
3,836,573 9/1974 Schreiber et al. ..................... 562/78

Primary Examiner—Werren B. Lone
Assistant Examiner—Vera C. Clarke
Attorney, Agent, or Firm—Depaoli & O'Brien

[57] ABSTRACT

A process for improving the rate of crystallization of a diphenylisophthalate/diphenylterephthalate monomer. The process comprises dissolving the monomer in an organic solvent, filtering the solution to remove impurities, and crystallizing the monomer to remove impurities. The precipitated monomer is then separated from the solvent by a centrifuge and dried. The monomer has a desired crystal size of about 2 mm. The process also is more efficient in that it reduces scaling inside the reactor system.

3 Claims, 1 Drawing Figure

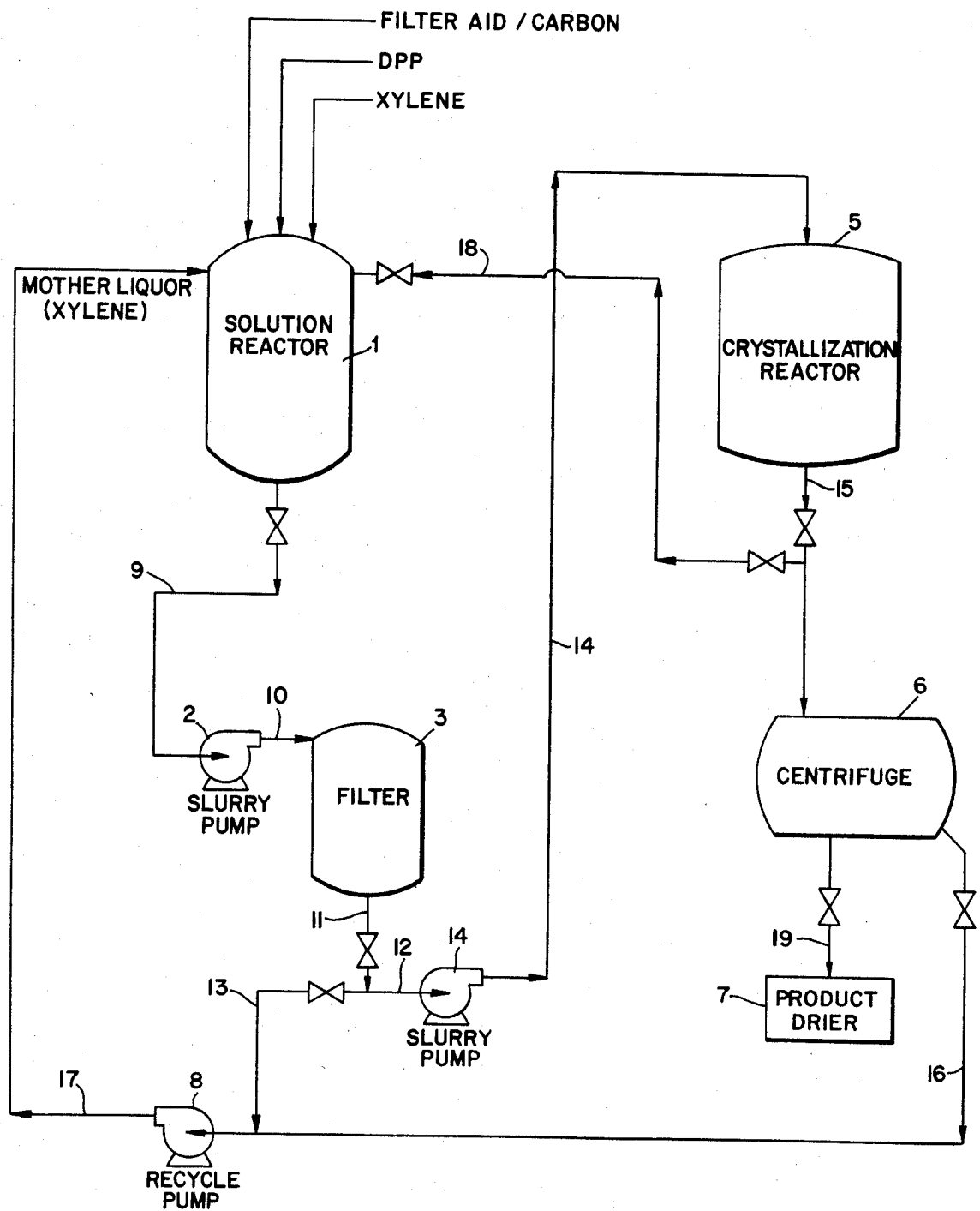

RATE OF CRYSTALLIZING DIPHENYLISOPHTHALATE/DIPHENYLTEREPHTHALATE MONOMER

This invention relates to crystallization of diphenylisophthalate/diphenylterephthalate monomer to obtain a particle size of about 2 mm. The process comprises the steps of dissolving the monomer in a solvent such as xylene or an equivalent thereof, treating the mixture with a filter aid to remove color contaminants, removing the filter aid by filtration and cooling the mixture to precipitate the monomer at a rate sufficient to obtain a crystal size of about 2 mm.

BACKGROUND OF THE INVENTION

Various processes of purification of aromatic dicarboxylic acids such as isophthalic acid and terephthalic acid are known in the prior art. U.S. Pat. No. 2,664,440, issued to Toland, discloses a process for separating isophthalic and terephthalic acids from the mixtures by dissolving the acids in a tertiary amine, crystallizing the dissolved salts, and then decomposing the salts to their respective acids. U.S. Pat. No. 2,881,548, issued to Ham et al, discloses a process for purifying aromatic dicarboxylic acids using a recrystallization solvent. The recrystallization solvent can be N,N-dimethylformamide, N,N-dimethylacetamide, mixtures of N,N-dimethylformamide and water, N,N-dimethylacetamide and water, N-N-dimethylformamide and methanol, and N,N-dimethylacetamide and methanol. U.S. Pat. No. 3,849,489, issued to Rudzki, discloses a process for purifying terephthalic acid by forming an ammonium terephthalate solution by reacting terephthalic acid in ammonia water, separating the ammonium terephthalate from the solution, and decomposing the ammonium terephthalate so as to produce terephthalic acid. The terephthalic acid is redissolved in ammonia water, the impurities in solution oxidized and the solution then filtered and contacted with activated charcoal. Ammonium terephthalate is separated from the process solution and decomposed to produce terephthalic acid. The formation of diphenylisophthalate/diphenylterephthalate monomer and other similar monomers can take place by various methods known in the prior art. U.S. Pat. No. 3,068,206, issued to Nicolson et al, discloses a polyester synthetic reaction system wherein one or more polyhydric alcohols such as ethylene or propylene glycol or glycerol are reacted with one or more polycarboxylic acids or their anhydrides. A modifying agent may or may not be used. The reaction is preferably carried out at temperatures from room temperaure to about 300° C. U.S. Pat. No. 3,039,980, issued to Mallison, discloses a polyhydric alcohol/polycarboxylic acid reaction wherein water of the esterification reaction is removed from the reaction zone by passing through the reaction zone an inert, organic, normally liquid solvent. U.S. Pat. No. 3,109,831, issued to Seiner, discloses reaction between a polyol and polyester of a dicarboxylic acid whereby the volatilization of the polyol is held to a minimum. U.S. Pat. No. 3,819,585, issued to Funk et al, discloses the formation of a polyester from ethylene glycol and terephthalic acid. The reaction has two phases wherein the first phase is conducted at a pressure of about 0-5 psig through about 74-95% of esterification, and the second phase is conducted at a substantially higher pressure than the first phase during which the percent of esterification is increased to about 95-99%. U.S. Pat. No. 4,146,729, issued to Goodley et al, discloses an esterification reaction between terephthalic acid and ethylene glycol whereby the excess glycol is recovered from reaction off-gases. U.S. Pat. No. 4,204,070, issued to Suzuki et al, discloses a process for preparing bis(hydroxyethyl)terephthalate where terephthalic acid is dissolved in molten bis(hydroxyethyl)terephthalate and its low molecular weight oligomers at a temperature above the dew point of ethylene glycol. Ethylene glycol is fed into the solution at a controlled rate so that the ethylene glycol does not distill off. U.S. Pat. No. 4,254,246, issued to Dicoi et al, discloses a reaction of ethylene glycol and terephthalic acid in the present of a catalyst so that the vapor by-products from the esterification, prepolycondensation and polycondensation stages are continuously rectified yielding high-purity ethylene glycol (99.85%) which is returned to the process.

U.S. Pat. No. 3,418,286, issued to Schmidt et al, discloses the reaction of a polyhydric alcohol and a carboxylic acid to produce a polyester resin by a fusion process. The reaction can be carried out at temperatures above 350° F. A vacuum or reduced pressure is also applied to the system, but not until the reaction has gone ⅓ of the way to completion and before the reaction has gone ¾ of the way to completion.

BRIEF DESCRIPTION OF THE INVENTION

The invention relates to increased rates of crystallization of diphenylisophthalate/diphenylterephthalate monomer by contacting the monomer with a solvent such as xylene, treating the solution with a filter aid to remove color-contaminants, filtering the solution to remove the filter aid, and cooling the solution to precipitate the monomer. The cooling is carried out at a rate sufficient to obtain a crystal size of 2 mm and to minimize scaling in the reactor system.

BRIEF DESCRIPTION OF THE DRAWING

The drawing illustrates diphenylisophthalate/diphenylterephthalate monomer crystallization process and apparatus.

DETAILED DESCRIPTION OF THE INVENTION

This invention deals with an increased rate of crystallization of a diphenylisophthalate/diphenylterephthalate monomer, hereinafter DPP monomer. The increased rate enables the production of a monomer of consistent crystal size (about 2 mm) and minimizes scaling on the walls, baffles and agitators of the reactors used in the crystallization process.

Referring to the drawing, the DPP monomer is placed in a solution reactor 1 with a filter aid such as activated carbon and/or diatomaceous earth, and a solvent, preferably xylene. Although xylene is a preferred solvent, other related inert organic solvents such as benzene, toluene, ethylbenzene, methyl cyclohexane, and cyclohexane may be used. Four to five pounds of DPP are used for every gallon of solvent. The concentration of filter aid will be less than about 5 wt.% and is usually about 1 wt.% for diatomaceous earth and about 2 wt.% for activated carbon. The solution is heated in reactor 1 to a temperature of about 130°-140° C. while being thoroughly mixed by an agitator. The solution leaves reactor 1 via line 9 and passes through a slurry pump 2 capable of obtaining a rate of 300 GPM and a head pressure of about 40 psig. The solution is then introduced into filter 3 through line 10. Preferably, the filter is a horizontal plate filter capable of removing the diatomaceous earth and/or activated carbon originally added to the DPP monomer and solvent. Removal can be accomplished by using a filter aid precoat such as diatomaceous earth in the filter to initiate formation of the solids cake. A filter cloth such as canvas or nylon should be used to act as a support for the diatomaceous earth. A flow rate of 260-280 GPM should be achieved when using this filter. A most preferred embodiment of the filter is the Niagara Batch-Mixer TM by Ametek.

After leaving filter 3 through lines 11 and 12, the solution passes through another slurry pump 4, which is essentially the same as slurry pump 2, and then through line 14 to crystallization reactor 5. After leaving filter 3, the solution also may be sent through line 13 to line 16 through pump 8, through line 17, and recycled to solution reactor 1. The crystallization reactor 5 is the same size as solution reactor 1 and both are jacket-type reactors, equipped with agitators, which are capable of achieving temperatures of 150° C. In crystallization reactor 5, the solution is cooled and crystallized. Upon completion, the crystallized monomer and solvent mixture are sent through line 15 to a centrifuge 6. The solution may be recycled through lines 15 and 18 to reactor 1. Centrifuge 6, which is a suspended batch or automatic batch type, removes the solvent from the crystallized monomer. The solvent passes through line 16 to recycle pump 8 which has a flow rate of about 300 GPM. The solution is then sent through line 17 for return to solution reactor 1. The crystallized DPP monomer is removed from the centrifuge and sent through line 19 to a product dryer 7. The dryer should be capable of mixing the material frequently and may be a rotary drum dryer or a screw-conveyor dryer.

The following example illustrates the best mode now contemplated for carrying out the invention.

EXAMPLE

Using the procedure described above, 4 to 5 pounds of DPP for every gallon of solvent are placed in solution reactor 1 with 1 wt.% diatomaceous earth and 2 wt.% activated carbon. This mixture passes through line 9 to slurry pump 2, through line 10 to filter 3, through lines 11 and 12 to slurry pump 4, and through line 14 to crystallization reactor 5.

The crystallization reactor 5 was preheated to a temperature of over 230° F. Upon transfer of the DPP solution to the crystallization reactor, the reactor was cooled over an approximately 10-hour time period. The time, jacket temperature of the reactor, internal temperature of the reactor, and agitator speed are listed below in the following table.

| Time | Jacket Temp. | Internal Temp. | Agitator Speed |
| --- | --- | --- | --- |
| 0450 | 230° F. | 190° F. | off |
| 0505 | 230° F. | 230° F. | slow |
| 0515 | 210° F. | 230° F. | slow |
| 0530 | 200° F. | 230° F. | slow |
| 0545 | 185° F. | 220° F. | slow |
| 0600 | 170° F. | 208° F. | slow |
| 0615 | 170° F. | 200° F. | fast |

-continued

| Time | Jacket Temp. | Internal Temp. | Agitator Speed |
| --- | --- | --- | --- |
| 0630 | 158° F. | 192° F. | fast |
| 0645 | 152° F. | 185° F. | fast |
| 0700 | 152° F. | 179° F. | fast |
| 0715 | 152° F. | 173° F. | fast |
| 0730 | 145° F. | 169° F. | fast |
| 0745 | 145° F. | 164° F. | fast |
| 0800 | 131° F. | 159° F. | fast |
| 0815 | 131° F. | 153° F. | fast |
| 0830 | 131° F. | 148° F. | fast |
| 0845 | 131° F. | 144° F. | fast |
| 0900 | 131° F. | 142° F. | fast |
| 0915 | 96° F. | 140° F. | fast |
| 0930 | 94° F. | 134° F. | fast |
| 0945 | 93° F. | 130° F. | fast |
| 1000 | 93° F. | 125° F. | fast |
| 1015 | 70° F. | 120° F. | fast |
| 1030 | 63° F. | 114° F. | fast |
| 1045 | 60° F. | 108° F. | fast |
| 1100 | 60° F. | 102° F. | fast |
| 1115 | 60° F. | 97° F. | fast |
| 1130 | 60° F. | 92° F. | fast |
| 1145 | 60° F. | 88° F. | fast |
| 1200 | 60° F. | 84° F. | fast |
| 1215 | 60° F. | 80° F. | fast |
| 1230 | 60° F. | 77° F. | fast |
| 1245 | 60° F. | 74° F. | fast |
| 1300 | 60° F. | 72° F. | fast |
| 1315 | 60° F. | 69° F. | fast |
| 1330 | 60° F. | 67° F. | fast |
| 1345 | 60° F. | 66° F. | fast |
| 1400 | 60° F. | 64° F. | fast |
| 1415 | 60° F. | 62° F. | fast |
| 1430 | 60° F. | 60° F. | fast |

The mixture is then passed through line 15 to centrifuge 6, where the DPP monomer is separated from the xylene solvent, and passed through line 19 to product drier 7. The xylene passes through line 16 to recycle pump 8, and then through line 17 to solution reactor 1.

The above example produced a desirable DPP monomer product having a crystal size of 2 mm. A substantial reduction in scaling in the reactor apparatus was also achieved.

What is claimed is:

1. A process for improving the rate of crystallization of a diphenylisophthalate/diphenylterephthalate monomer and producing said monomer with a crystal size of about 2 mm comprising the steps of:
   a. dissolving said monomer in an organic solvent in the presence of filtration aids selected from the group consisting of diatomaceous earth, activated carbon, and mixtures thereof;
   b. filtering and removing said filtration aids to provide a filtered crystallization solution;
   c. introducing said filtered solution to a heated crystallization zone;
   d. cooling said crystallization solution to precipitate crystallized monomer from the solvent;
   e. centrifuging said crystallized monomer to remove solvent from the crystallized monomer; and
   f. thereafter drying said crystallized monomer.

2. The process of claim 1 wherein said organic solvent is selected from the group consisting of xylene, benzene, toluene, ethyl benzene, methyl cyclohexane, and cyclohexane.

3. The process of claim 2 wherein said organic solvent is xylene.

* * * * *